United States Patent [19]

McGahren et al.

[11] Patent Number: 4,977,143

[45] Date of Patent: Dec. 11, 1990

[54] ANTIBACTERIAL AND ANTITUMOR AGENTS LL-E33288EPSILON-I AND LL-E33288EPSILON-BR

[75] Inventors: William J. McGahren, Demarest, N.J.; George A. Ellestad, Pearl River, N.Y.

[73] Assignee: American Cyanamid Company, Stamford, Conn.

[21] Appl. No.: 161,627

[22] Filed: Feb. 29, 1988

[51] Int. Cl.$^5$ .................... A61K 31/71; C12P 19/26; C07H 5/00
[52] U.S. Cl. ....................... 514/25; 514/27; 514/867; 435/74; 435/75; 536/16.8; 536/16.9; 536/17.5; 536/18.4; 536/122
[58] Field of Search .............. 536/16.8, 16.9, 17.5, 536/17.6, 18.1, 18.4, 122; 435/7 A, 75, 867; 514/29, 25, 27

[56] References Cited

U.S. PATENT DOCUMENTS

| | | | |
|---|---|---|---|
| 4,346,075 | 8/1982 | Tomita et al. | 536/16.8 |
| 4,371,622 | 1/1983 | Jarai et al. | 435/867 |
| 4,440,751 | 4/1984 | Waltz et al. | 514/521 |
| 4,626,503 | 12/1986 | Lee et al. | 435/75 |

FOREIGN PATENT DOCUMENTS 0182152  5/1986
60-20598  2/1981  Japan.

OTHER PUBLICATIONS

Lee et al., Am. Chem. Soc. 109:3464–3468 (1987).
Schreiber et al., J. Am. Chem. Soc. 110:631–633 (1988).

*Primary Examiner*—Ronald W. Griffin
*Assistant Examiner*—Nancy S. Carson
*Attorney, Agent, or Firm*—Thomas S. Szatkowski

[57] ABSTRACT

Antibacterial and antitumor agents designated LL-E33288$\epsilon$-I and LL-E33288$\epsilon$-Br and their production by strains of *Micromonospora echinospora* ssp. *calichensis* designated NRRL-15839, NRRL-15975 and NRRL-18149, are disclosed.

10 Claims, 2 Drawing Sheets

ANTIBACTERIAL AND ANTITUMOR AGENTS LL-E33288EPSILON-I AND LL-E33288EPSILON-BR

BACKGROUND OF THE INVENTION

The family of antibacterial and antitumor agents, known collectively as the LL-E33288 complex, are described and claimed in a series of related, commonly-assigned U.S. Pat. applications, namely Ser. No. 672,031, filed Nov. 16, 1984 (now abandoned); Ser. No. 787,066, filed Oct. 17, 1985 (now abandoned); and Ser. No. 9,321, filed Jan. 30, 1987.

These applications describe the LL-E33288 complex, the components thereof, namely LL-E33288$\alpha_1$-Br, LL-E3328$\alpha_1$-I, LL-E33288$\alpha_2$-Br, LL-E33288$\alpha_2$-I, LL-E33288$\alpha_3$-Br, LL-E33288$\alpha_3$-I, LL-E33288$\alpha_4$-Br, LL-E33288$\beta_1$-Br, LL-E33288$\beta_1$-I, LL-E33288$\beta_2$-Br, LL-E33288$\beta_2$-I, LL-E33288$\gamma_1$-Br, LL-E332887$\gamma_1$-I, and LL-E33288$\delta_1$-I, and methods for their production by aerobic fermentation utilizing a new strain of *Micromonospora echinospora* ssp *calichensis* or natural or derived mutants thereof.

SUMMARY OF THE INVENTION

This invention is concerned with a new component, LL-E33288$\epsilon$ derived by aerobic fermentation of the new strain of *Micromonospora echinospora* ssp *calichensis* or natural or derived mutants thereof. LL-E33288$\epsilon$ has antibacterial and antitumor activity.

Since, as is the case with other components of the LL-E33288 complex, iodine containing components are found only in fermentations using media containing inorganic or organic iodide, while bromine containing components are found only in fermentations using media containing inorganic or organic bromine, this invention encompasses both LL-E33288$\epsilon$-I, the iodine containing component and LL-E33288$\epsilon$-Br, the bromine containing component.

BRIEF DESCRIPTION OF THE DRAWINGS

FIG. I is the proton magnetic resonance spectrum of LL-E33288$\epsilon$-I.

FIG. II is the carbon-13 magnetic resonance spectrum of LL-E33288$\epsilon$-I.

DESCRIPTION OF THE INVENTION

Figure 1:
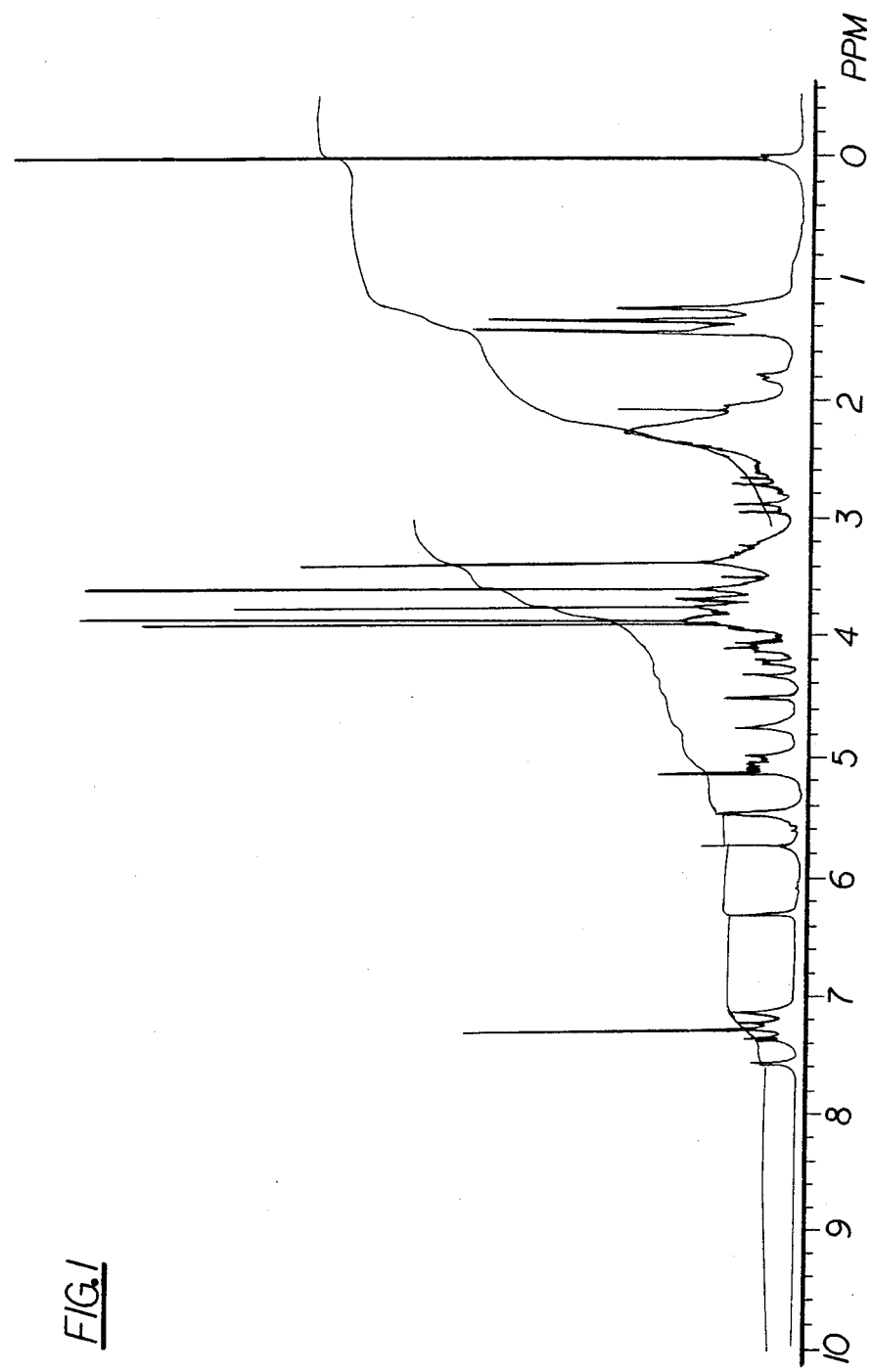
Figure 2:
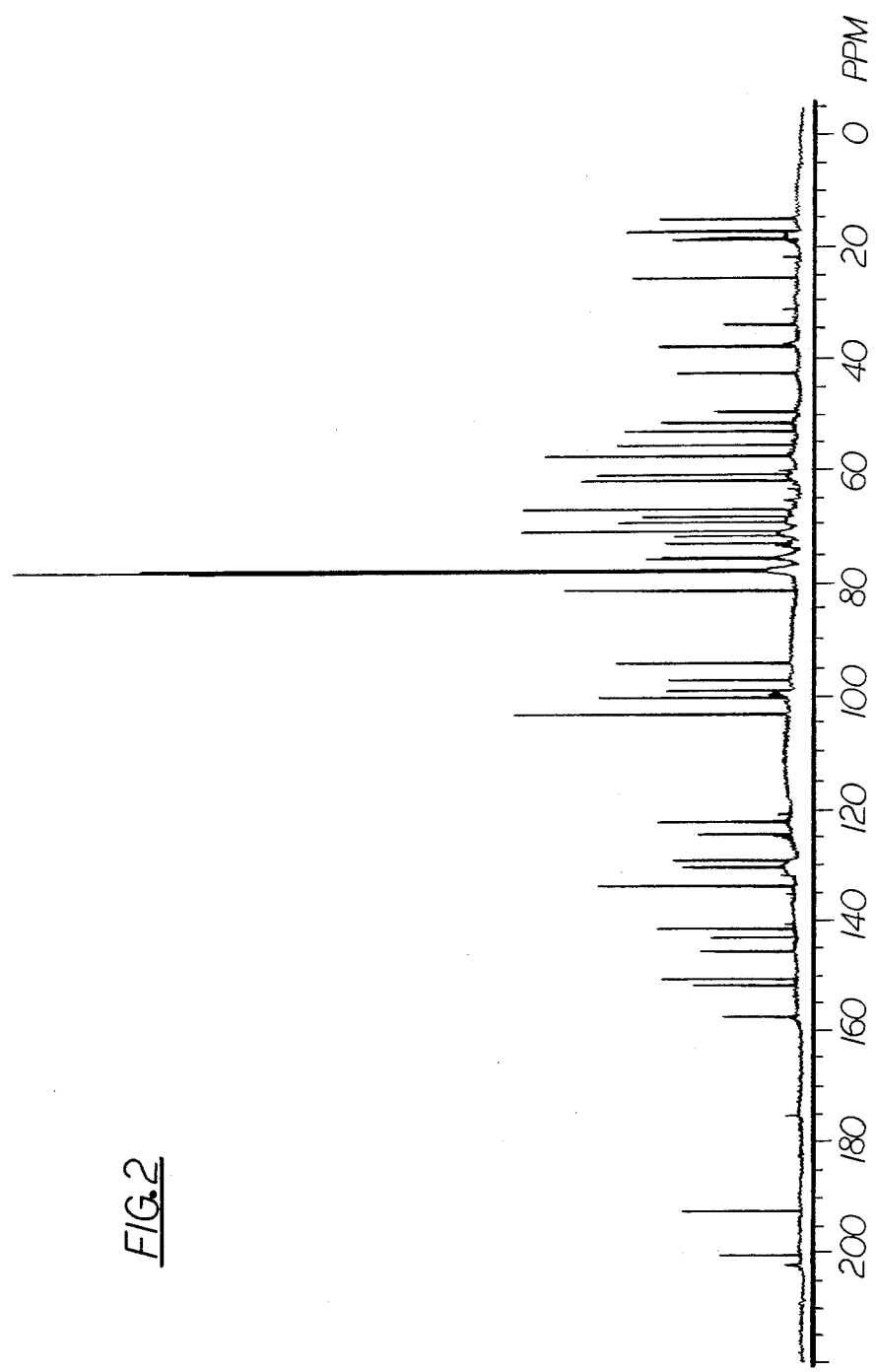

The physico-chemical characteristics of LLE33288$\epsilon$-I are described below:

(a) Molecular formula: $C_{54}H_{74}N_3O_{21}IS_2$;
(b) Elemental analysis: C, 48.37; H, 5.72; N, 3.04; S, 4.98 and I, 9.28;
(c) Optical rotation: $[\alpha]_D^{25} = -14 \pm 1°$ (C, 1.115%, methanol);
(d) Optical density: 0.23 at 10$\mu$g/ml in methanol at 230 nm;
(e) Proton magnetic resonance spectrum: as shown in FIG. I (300 MHz, CDCl$_3$), with significant peaks at 7.16 (doublet), 7.21 and 7.26 (triplets) and 7.55ppm (doublet); and
(f) Carbon-13 magnetic resonance spectrum: as shown in FIG. II (75.46 MHz, CDCl$_3$), with significant peaks in the regions of 120–160 and 190–210 ppm.

While the structures of LL-E33288$\epsilon$-I and Br have not been fully elucidated, a proposed structure for LLE33288$\epsilon$-I is given below.

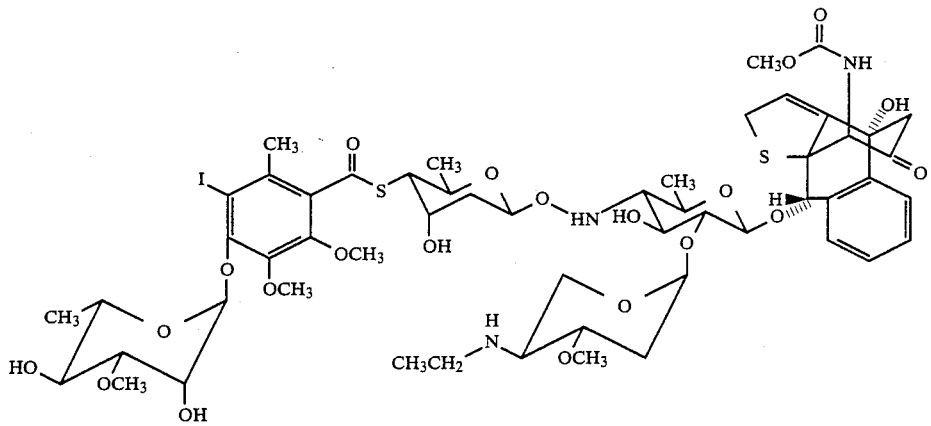

The new antibacterial and antitumor agents LL-E33288$\epsilon$-I and LL-E33288$\epsilon$-Br are formed during the cultivation, under controlled conditions of *Micromonospora echinospora* ssp *calichensis* NRR1 15839, 15975 and 18149.

These new microorganisms are maintained in the culture collection of the Medical Research Division, American Cyanamid Company, Pearl River, NY as culture numbers LL-E33288(NRRL 15839), LL-E33288-R66 (NRRL 15975) and LL-E33288 UV 784 (NRRL 18149). Viable cultures of these new microorganisms have been deposited with the Culture Collection Laboratory, Northern Regional Research Center, U.S. Department of Agriculture, Peoria, Ill. and have been added to its permanent collection. Access to said cultures under the above NRRL strain designations, during pendency of the instant application shall be available to one determined by the Commissioner of Patents and Trademarks to be entitled thereto under 37 C.F.R. 1.14 and 35 U.S.C. 122, and all restrictions on availability to the public of such cultures will be irrevocably removed upon grant of a patent on the instant application.

Culture LL-E33288 (NRRL 15839) was isolated from a caliche clay soil sample collected in Texas. Cultures LL-E33288-R66(NRRL 15975) and LL-E33288 UV 784 (NRRL 18149) were obtained as hereinafter described.

The generic assignment of NRRL 15839 to the genus *Micromonospora* was confirmed morphologically and chemically. The strain produces monospores either singly or in masses on the vegetative hyphae. No aerial hyphae were observed. Electron microscopic examination showed that the spores were warty. Whole cell analysis showed that the strain contained the meso isomer of diaminopimelic acid. The 3-OH derivative of diaminopimelic acid was present in large (major) amounts. Additionally the strain showed the presence of xylose plus traces of arabinose in its whole cell sugar hydrolysates (whole cell sugar pattern of Type D).

From macromorphological and physiological studies it was concluded that NRRL 15839 can be considered a subspecies of *M. echinospora* (it is closest to *M. echinospora* ssp. *pallida*). Data on the morphology of NRRL 15839 are given in Tables I and II. Physiological data are given in Tables III and IV.

TABLE I

Macromorphology of NRRL 15839 (Colors are NBS-ISCC)

| ISP Agar Medium | Spores | Vegetative Mycelium | Soluble Pigments |
|---|---|---|---|
| Yeast-Malt (ISP 2) | — | Dark orange-yellow (72) | — |
| Oatmeal (ISP 3) | — | Colorless to pale orange-yellow (73) | — |
| Inorganic Salts-Starch (ISP 4) | Slight border of black spores | Dark orange-yellow (72) to light yellow-brown (76) | Light brownish |
| Glycerol-Asparagine (ISP 5) | — | Pale orange-yellow (73) to colorless | — |

TABLE II

Macromorphology of NRRL 15839 on Various Agar Media Used for Actinomycete Growth (28°, 2 weeks)

| Agar Medium | NRRL 15839 |
|---|---|
| Pablum | Beige vegetative hyphae; Slight black spores; No soluble pigment |
| Yeast Czapek's | Beige vegetative hyphae; No spores; No soluble pigment |
| Czapek's | Beige vegetative hyphae; Slight black spores; No soluble pigment |
| Yeast Dextrose | Tan vegetative hyphae; Moderate black spores; Slight dark pigment |
| Nutrient | Colorless to tan vegetative hyphae; Slight black spores; No soluble pigment |
| Nutrient Glycerol | Colorless to light beige vegetative hyphae; No spores; No soluble pigment |
| Bennett's Dextrin | Colorless to beige vegetative hyphae; Slight black spores; Slight rose-brown pigment |
| Glucose Asparagine | Colorless to light orange-beige vegetative hyphae; No spores; No soluble pigment |

TABLE III

Carbohydrate Utilization of NRRL 15839

| | |
|---|---|
| Arabinose | + |
| Cellulose | — |
| Fructose | + |
| Glucose | + |
| Inositol | — |
| Mannitol | — |
| Raffinose | ± |
| Rhamnose | + |
| Sucrose | + |
| Xylose | + |

TABLE IV

Physiological Reactions of NRRL 15839

| | |
|---|---|
| Hydrolysis of | |
| Casein | + |
| Xanthine | — |
| Hypoxanthine | — |
| Tyrosine | + |
| Adenine | — |
| Gelatin | + |
| Potato Starch | + |
| Esculin | + |
| Production of | |
| Nitrate Reductase | + |
| Phosphatase | weak |
| Urease | — |
| Growth on | |
| Salicin | — |
| 5% Sodium Chloride | — |
| Lysozyme Broth | — |
| Decarboxylation of | |
| Acetate | + |
| Benzoate | — |
| Citrate | — |
| Lactate | — |
| Malate | — |
| Mucate | — |
| Oxalate | — |
| Propionate | + |
| Pyruvate | + |
| Succinate | — |
| Tartrate | — |
| Acid from | |
| Adonitol | — |
| Arabinose | + |
| Cellobiose | + |
| Dextrin | + |
| Dulcitol | — |
| Erythritol | — |
| Fructose | + |
| Galactose | variable |
| Glucose | + |
| Glycerol | — |
| Inositol | — |
| Lactose | — |
| Maltose | + |
| Mannitol | — |
| Mannose | + |
| α-Methyl-D-glucoside | — |
| Melibiose | — |
| Raffinose | + |
| Rhamnose | + |
| Salicin | + |
| Sorbitol | — |
| Sucrose | + |
| Trehalose | + |
| Xylose | + |
| β-Methyl-D-xyloside | — |
| Growth at | |
| 10° C. | — |
| 42° C. | + |
| 45° C. | + |

+ = positive; — = negative

Two antibiotic-producing mutants were derived from the original culture LL-E33288 (NRRL 15839) in accordance with the following description and diagram. The original culture LL-E33288 (NRRL 15839) was plated and 50 single colonies were isolated. These were designated NS1 to NS50 (NS=natural selection).

Fermentation of these isolates showed that those with moderate sporulation were generally better producers of the LL-E33288 complex. Isolate NS6 was selected as representative of this group.

Using isolate NS6 as the starting culture, spore suspensions were prepared and exposed to various mutagens. From a series of exposures to ultraviolet irradiation, single colonies were obtained, from which isolate UV610 was selected as a high yielding mutant. Isolate UV610 was streaked and subisolates 1 to 7 were obtained. Subisolate UV610(3) was selected for further work.

Vegetative growth from isolate UV610(3) (see following diagram) was prepared as employed for fermentation and used to inoculate a flask of medium consisting of peptone, dextrose, molasses and water. This medium was supplemented with LL-E33288$\beta_1$-Br at a concentration of 8 $\mu$g/ml. A number of platings were done from this flask and a resistant population was obtained on the seventh day. A total of 97 colonies (R1 to R97) were isolated. Isolate R66 was subsequently deposited as NRRL 15975.

Isolate R80, which is essentially similar to R66 in its biosynthetic potential, was used as the starting culture from which a spore suspension was prepared and exposed to relatively high concentrations of the LL-E33288 complex, in order to obtain higher yielding isolates which were resistant to the LL-E33288 antibiotics One survivor, labeled T2, did produce higher yields of LL-E33288$\beta_1$-Br and LL-E332887$\gamma_1$-I in flask fermentations. A spore suspension of T2 was prepared and exposed to ultraviolet irradiation. A total of 131 colonies were then isolated (UV703 to UV834), fermented and assayed. Isolate UV784 was selected for its relatively high yield and was subsequently deposited as NRRL 18149.

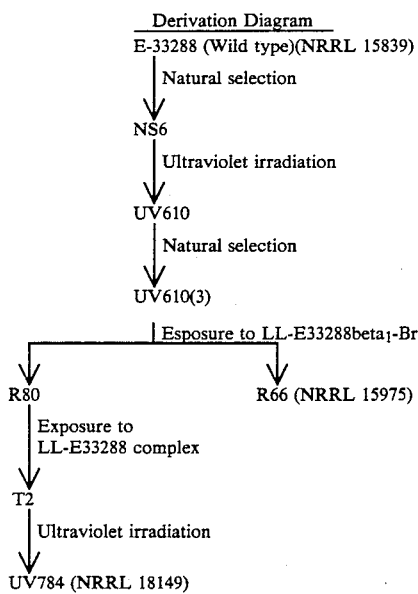

It is to be understood that of the production of LL-E33288$\epsilon$I and LL-E33288$\epsilon$-Br, the present invention is not limited to the above described organisms or to organisms fully answering the above growth and microscopic characteristics which are given for illustrative purposes only. In fact, it is desired and intended to include the use of mutants produced from these organisms by various means such as exposure to x-radiation, ultraviolet radiation, N'-methyl-N'-nitroN-nitrosoguanidine, actinophages and the like.

The in vitro antibacterial activity of LL-E33288$\epsilon$-I was determined against a spectrum of grampositive and gram-negative bacteria by a standard agar dilution method. Mueller-Hinton agar containing two-fold decreasing concentrations of the antibiotic were poured into petri plates. The agar surfaces were inoculated with 1 to $5 \times 10^4$ colony forming units of bacteria by means of a Steers replicating device. The lowest concentration of LL-E33288$\epsilon$-I that inhibited growth of a bacterial strain after about 18 hours growth at 35° C. was recorded as the minimal inhibitory concentration (MIC) for that strain. The results appear in Table V.

TABLE V

In vitro Antibacterial Activity of LL-E33288$\epsilon$-I

| Organism | | Minimal Inhibitory Concentration ($\mu$g/ml) |
|---|---|---|
| Escherichia coli | CMC 84-11 | >64 |
| Escherichia coli | No. 311-(MP) | >64 |
| Escherichia coli | ATCC 25922 | >64 |
| Klebsiella pneumoniae | CMC 84-5 | >64 |
| Klebsiella pneumoniae | AD (MP) | >64 |
| Enterobacter cloacae | CMC 84-4 | >64 |
| Enterobacter aerooenes | IO 83-44 | >64 |
| Serratia marcescens | CMC 83-27 | >64 |
| Serratia marcescens | F 35 (MP) | >64 |
| Morganella morganii | IO 83-18 | >64 |
| Providencia stuartii | CMC 83-82 | >64 |
| Citrobacter diversus | K 82-24 | >64 |
| Citrobacter freundii | IO 83-13 | >64 |
| Acinetobacter sp | CMC 83-89 | >64 |
| Acinetobacter sp | IO 83-49 | >64 |
| Pseudomonas aeruginosa | 12-4-4 (MP) | >64 |
| Pseudomonas aeruginosa | ATCC 27853 | >64 |
| Staphylococcus aureus | Smith | 4 |
| Staphylococcus aureus | SSC 82-21 | 4 |
| Staphylococcus aureus | ATCC 25923 | 4 |
| Staphylococcus aureus | SSC 82-20 | 4 |
| Staphylococcus aureus | SSC 82-23 | 4 |
| Staphylococcus aureus | SSC 82-24 | 4 |
| Staphylococcus aureus | SSC 82-54 | 4 |
| Staphylococcus epidermidis | CMC 83-133 | 4 |
| Staphylococcus epidermidis | ATCC 12228 | 4 |
| Streptococcus faecalis | ATCC 29212 | 4 |
| Streptococcus faecalis | VGH 84-65 | 4 |
| Streptococcus faecalis | CMC 83-53 | 4 |
| Streptococcus faecalis | UCI 85-20 | 4 |
| Streptococcus faecalis | IO 83-28 | 4 |

Certain in vivo testing systems and protocols have been developed by the National Cancer Institute for testing compounds to determine their suitability as antineoplastic agents. These have been reported in "Cancer Chemotherapy Reports", Part III, Volume 3, No. -2 (1972), Geran, et al. These protocols have established standardized screening tests which are generally followed in the field of testing for antitumor agents. Of these systems, lymphocytic leukemia P388 is particularly significant to the present invention. This neoplasm is utilized for testing as transplantable tumors in mice. Significant antitumor activity shown in this protocol by a percentage increase of mean survival times of the treated(T) animals over the control(C) animals is indicative of similar results in human leukemias and solid tumors.

LYMPHOCYTIC LEUKEMIA P388 Test

The animals used were BDF1 mice, all of one sex, weighing a minimum of 17 g and all within a 3 g weight range. There were 5 or 6 mice per test group. The tumor transplant was by intraperitoneal injection of 0.5 ml of dilute ascitic fluid containing $10^6$ cells of lymphocytic leukemia P388. The test compound was administered intraperitoneally at a volume of 0.5 ml in 0.2% Klucel in normal saline on days 1, 5 and 9 (relative to tumor inoculation) at the indicated doses. The mice were weighed and survivors recorded on a regular basis for 30 days. The median survival time and the ratio of survival time for treated(T)/control(C) animals were calculated. The positive control compound was 1,4-dihydroxy-5,8-bis[[2-(2-hydroxyethylamino)ethyl]amino]anthraquinone, dihydrochloride (U.S. Pat. No. 4,197,249), given as an intraperitoneal injection in 0.5 ml of 0.2% Klucel on days 1, 5 and 9 at the indicated doses. The results appear in Table VI.

If T/C X 100 (%) is 125 or over, the tested compound is considered to have significant anti-tumor activity.

TABLE VI

Lymphocytic Leukemia P388 Test

| Compound | Dose (mg/kg) | Median Survival (Days) | T/C × 100 (%) |
|---|---|---|---|
| LL-E33288ε-I | 3.2 | 12 | 120 |
|  | 1.6 | 16.5 | 165 |
|  | 0.8 | 17.5 | 175 |
|  | 0.4 | 15.5 | 155 |
|  | 0.2 | 15.5 | 155 |
|  | 0.1 | 15 | 150 |
|  | 0.05 | 13 | 130 |
| Control | — | 10 | — |
| Positive Control | 1.6 | 27 | 270 |
|  | 0.8 | >30 | >300 |
|  | 0.4 | 21.5 | 215 |

The invention is further illustrated by the Examples set forth below which are not intended to limit the invention.

Example 1

Inoculum Preparation

A typical medium used to grow the primary inolculum was prepared according to the following formula:

| | |
|---|---|
| Dextrin | 2.4% |
| Glucose | 0.5% |
| Yeast extract | 0.5% |
| Tryptone | 0.5% |
| Beef extract | 0.3% |
| Calcium carbonate | 0.4% |
| Antifoam agent | 0.3% |
| Water | balance to 100% |

This medium was sterilized and a 100 ml portion in a flash inoculated with mycelia of the culture NRRL 18149. This medium was placed on a rotary shaker and agitated vigorously for 48 hours at 32° C. This primary inoculum was then used to inoculate 10 liters of the above sterile medium in a bottle. This medium was agitated at 32° C. for 48 hours providing secondary inoculum. This secondary inoculum was then used to inoculate 300 liters of the above sterile medium in a tank which was incubated at 32° C. for 48 hours with agitation by an impeller driven at 220 rpm and a sterile air flow of 200 liters per minute, providing tertiary inoculum.

Example 2

Tank Fermentation

A fermentation medium was prepared according to the following formula:

| | |
|---|---|
| Sucrose | 2.0% |
| Ferric sulfate heptahydrate | 0.01% |
| Magnesium sulfate heptahydrate | 0.02% |
| Peptone | 0.5% |
| Molasses | 0.5% |
| Potassium iodide* | 0.05% |
| Calcium carbonate | 0.5% |
| Antifoam agent | 0.3% |
| Water | balance to 100% |

*Substitution of potassium bromide will result in the production of bromo derivatives.

A 2700 liter portion of the above medium was sterilized and then inoculated with 300 liters of tertiary inoculum prepared as described in Example 1. Aeration was supplied at the rate of 6.5 liters of sterile air per liter of mash per minute and agitation was supplied by an impeller driven at 120 rpm. The temperature was maintained at 30° C. and the fermentation was terminated after about 125 hours, at which time the mash was harvested.

Example 3

Isolation of LL-E33288ε-I

A total of 2400 liters of mash from fermentations conducted as described in Example 2 was agitated for one hour with an equal volume of ethyl acetate. The resulting emulsion was filtered through diatomaceous earth in a press. The ethyl acetate phase was separated, evaporated to about 200 liters under reduced pressure and adjusted to pH 6 to 7 with 1N sodium hydroxide. The ethyl acetate phase was separated and concentrated to 30–40 liters, then diluted with 30 liters of water to ease the emulsion, agitated and then allowed to settle, forming three phases. The aqueous (bottom phase) was separated and extracted with ethyl acetate. This extract was combined with the clear (upper) solvent phase and concentrated to about 6 liters.

The 6 liters of oily suspension was divided into 1 liter portions, each of which was concentrated to an oil and defatted by partitioning between hexane and methanol. The methanol phases were evaporated to an oil stage and then combined. This oil was reconstituted in dichloromethane, charged on 2 kg of silica gel in a 12 inch bed column and developed using 4 liters of dichloromethane, followed by 4 liters each of 2.5% methanol in dichloromethane and 5% methanol in dichloromethane. One liter fractions were collected every 20 minutes. The activity was found in fractions 9 to 14 by biochemical induction assay. These fractions were combined and evaporated to 24 g of crude dark brown solid.

This solid was divided into 4 portions of about 6 g each. Each portion was stirred in 100 ml of acetonitrile for 30 minutes, then filtered. The filtrate was diluted with 150 ml of 0.2M ammonium acetate solution and refiltered. This filtrate was pumped onto a Waters L/C 500 instrument containing a Prepak reverse phase cartridge, which had been equilibrated with acetonitrile:0.2M ammonium acetate solution (45:55). The column was developed using 7 to 8 liters of the same solvent. The elution process was monitored at 254 nm. The second liter of eluate contained LL-E33288ε-I. This eluate was evaporated sufficiently to remove the bulk acetonitrile. The remaining aqueous suspension was extracted with one half its volume of ethyl acetate. The ethyl acetate extract was dried over anhydrous magnesium sulfate, concentrated to 10–20 ml and dripped into 75 ml of vigorously stirred hexane. The resulting precipitate was collected and dried, giving 1.694 g of LL-E33288ε-I.

Example 4

Purification of LL-E33288ε-I

A 1.69 g portion of the LL-E33288ε-I from Example 3 was rechromatographed on a Prepak reverse phase column using the solvent system acetonitrile:0.2M ammonium acetate solution (37:63). The core fractions of the symmetrical peak were taken and processed, giving 960 mg of off-white solid.

An 880 mg portion of the above solid was subjected to reverse phase preparative chromatography using the same developing solvent solution. The main peak of the monitored profile was shaved in two portions. The front fraction was processed, giving 186 mg of pure LL-E33288ε-I.

We claim:
1. The compound LL-E33288ε-I, having:
   (a) a molecular formula: $C_{54}H_{74}N_3O_{21}IS_2$;
   (b) an elemental analysis: C, 48.37; H, 5.72; N, 3.04; S, 4.98 and I, 9.28;
   (c) an optical rotation $[\alpha]_D^{25} = -14 \pm 1°$ (C, 1.115%, methanol);
   (d) an optical density: 0.23 at 10μg/ml in methanol at 230 nm;
   (e) a proton magnetic resonance spectrum as shown in FIG. I of the drawings;
   (f) a carbon-13 magnetic resonance spectrum: as shown in FIG. II of the drawings; and
   (g) The structure:

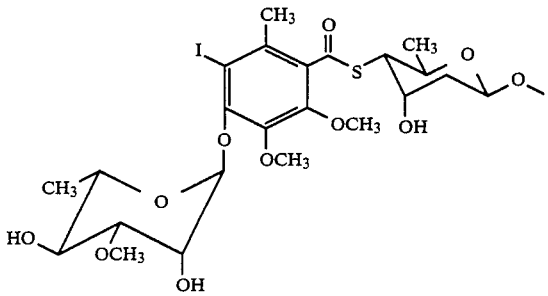

2. A process for producing the antibiotic LL-E33288εBr having the structure:

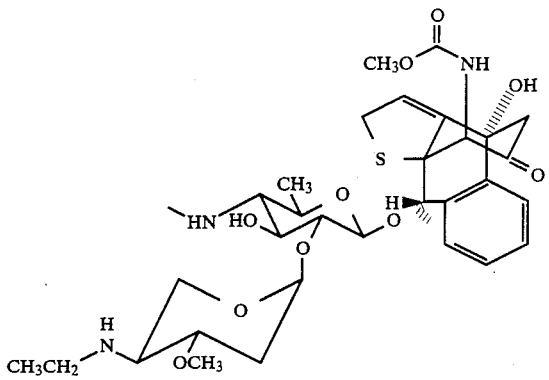

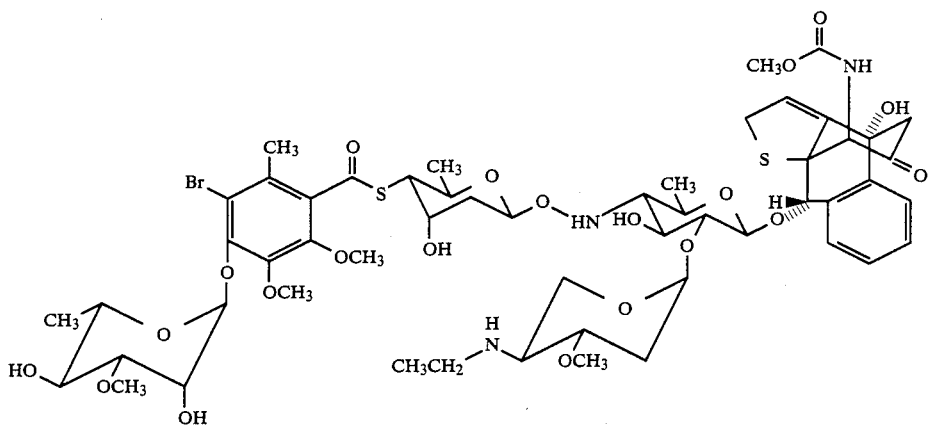

which comprises aerobically fermenting the organism *Micromonospora echinospora* ssp *calichensis* NRRL 15839 or its antibiotic-producing mutants NRRL 15975 or NRRL 18149 in a liquid medium containing assimilable sources of carbon, nitrogen, bromine and inorganic salts, until substantial antibiotic activity is imparted to said medium and then recovering the antibiotic therefrom.

3. A process according to claim 2, wherein the organism is *Micromonospora echinospora* ssp *calichensis* NRRL 18149.

4. The compound LL-E33288ε-Br having the structure:

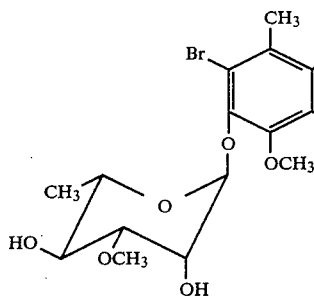
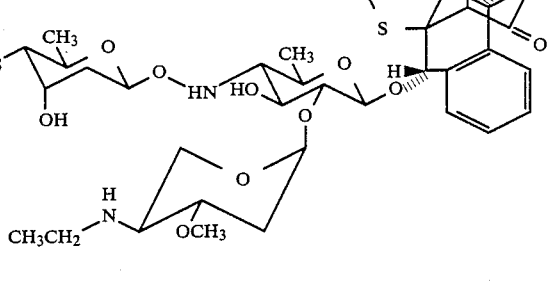

when prepared by the process of claim 2.

5. A process for producing antibiotic LL-E33288ε-I as recited in claim 1, which comprises aerobically fermenting the organism *Micromonospora echinospora* ssp *calichensis* NRRL 15839 or its antibiotic producing mutants NRRL 15975 or NRRL 18149 in a liquid medium containing assimilable sources of carbon, nitrogen, iodine and inorganic salts, until substantial antibiotic activity is imparted to said medium and then recovering the antibiotic therefrom.

6. A process according to claim 5, wherein the organism is *Micromonospora enchinospora* ssp *calichensis* NRRL 18149.

7. A process as recited in any of claims 2, 3, 5 and 6 which further comprises aerobically fermenting at a temperature of 24°–32° C. for a period of 90–200 hours.

8. A method of treating bacterial infections in a warm-blooded animal which comprises administering to said animal an antibacterially effective amount of a compound as set forth in either of claim 1 or 4 selected from the group consisting of LL-E33288ε-I and LL-E33288ε-Br.

9. A method of inhibiting the growth of tumors susceptible to treatment with a compound selected from the group consisting of LL-E33288ε-I and LL-E33288ε-Br in warm blooded animal which comprises administering to said animal a tumor inhibiting amount of a compound as set forth in either of claims 1 or 4.

10. A method of regressing leukemia in a warm blooded animal which comprises administering to said animal an anti leukemia amount of a compound as set forth in either of claims 1 or 4 selected from the group consisting of LL-E33288ε-I and LL-E33288ε-Br.

* * * * *